US011950896B2

(12) United States Patent
    Chase

(10) Patent No.: US 11,950,896 B2
(45) Date of Patent: Apr. 9, 2024

(54) BLOOD GLUCOSE TRACKING SYSTEM

(71) Applicant: Arnold Chase, West Hartford, CT (US)

(72) Inventor: Arnold Chase, West Hartford, CT (US)

( * ) Notice: Subject to any disclaimer, the term of this patent is extended or adjusted under 35 U.S.C. 154(b) by 859 days.

(21) Appl. No.: 16/856,100

(22) Filed: Apr. 23, 2020

(65) Prior Publication Data

US 2020/0245892 A1   Aug. 6, 2020

Related U.S. Application Data

(62) Division of application No. 16/118,827, filed on Aug. 31, 2018, now Pat. No. 10,631,753.
(Continued)

(51) Int. Cl.
    *A61B 5/0507*     (2021.01)
    *A61B 5/00*       (2006.01)
    (Continued)

(52) U.S. Cl.
    CPC .......... *A61B 5/0507* (2013.01); *A61B 5/0004* (2013.01); *A61B 5/14532* (2013.01);
    (Continued)

(58) Field of Classification Search
    CPC . A61B 5/0507; A61B 5/0004; A61B 5/14532; A61B 5/1495; A61B 5/6824;
    (Continued)

(56) References Cited

U.S. PATENT DOCUMENTS 7,613,488 B1   11/2009   Maracas et al.
2008/0200790 A1   8/2008   Kim et al.
(Continued)

FOREIGN PATENT DOCUMENTS

CN   205126252 U   4/2016
EP   2 425 770 A1   3/2012
(Continued)

OTHER PUBLICATIONS

Japanese Decision of Refusal and its English translation for corresponding JP Application No. 2020-551393 dated May 17, 2022.
(Continued)

*Primary Examiner* — Christian Jang
(74) *Attorney, Agent, or Firm* — McCormick, Paulding & Huber PLLC

(57) ABSTRACT

A blood glucose tracking system and method measures emitted microwave energy transmitted to and accepted by blood vessels in a desired target area of a patient in order to determine, in real time and in vivo, appropriate blood glucose levels. A measurement unit comprises a transmitter operatively connected to an antenna to deliver energy towards appropriate subcutaneous blood vessels. The measurement unit determines an accepted energy power value in the blood vessels associated with the desired target area. This measurement energy power value is compared with a calibration value, and the difference is used to determine a resultant blood glucose value. The determined blood glucose value may further be acclimatized using additional sensed values compensating for biological and ambient factors relevant to the patient. The final determined blood glucose value can be displayed for reading and/or transmitted and stored for recording for further reference.

18 Claims, 4 Drawing Sheets

Related U.S. Application Data

(60) Provisional application No. 62/646,510, filed on Mar. 22, 2018.

(51) Int. Cl.
*A61B 5/145* (2006.01)
*A61B 5/1495* (2006.01)

(52) U.S. Cl.
CPC .......... *A61B 5/1495* (2013.01); *A61B 5/6824* (2013.01); *A61B 5/7246* (2013.01); *A61B 5/742* (2013.01); *A61B 2562/0228* (2013.01)

(58) Field of Classification Search
CPC .................. A61B 5/7246; A61B 5/742; A61B 2562/0228
See application file for complete search history.

(56) References Cited

U.S. PATENT DOCUMENTS

| | | | |
|---|---|---|---|
| 2008/0319285 A1* | 12/2008 | Hancock | A61B 5/05 600/430 |
| 2008/0319434 A1* | 12/2008 | Rick | A61B 18/18 606/33 |
| 2010/0114086 A1 | 5/2010 | Deem et al. | |
| 2013/0297223 A1* | 11/2013 | Fischer | G16B 45/00 702/21 |
| 2014/0273821 A1* | 9/2014 | Miller | H04W 12/06 455/39 |
| 2016/0192867 A1 | 7/2016 | Esenaliev | |
| 2016/0317060 A1 | 11/2016 | Connor | |
| 2016/0317070 A1 | 11/2016 | Sivaraman et al. | |
| 2017/0156645 A1 | 6/2017 | Lin et al. | |
| 2018/0020948 A1 | 1/2018 | Butterworth et al. | |
| 2018/0325431 A1 | 11/2018 | Guarin et al. | |

FOREIGN PATENT DOCUMENTS

| | | | |
|---|---|---|---|
| GB | 2428093 | A | 1/2007 |
| JP | 2009500096 | A | 1/2009 |
| JP | 2010524589 | A | 7/2010 |
| JP | 2010169396 | A | 8/2010 |
| JP | 2017536147 | A | 12/2017 |
| KR | 20090084409 | A | 8/2009 |
| KR | 20150095602 | A | 8/2015 |
| KR | 20170058187 | A | 5/2017 |
| WO | 2007003955 | A1 | 1/2007 |
| WO | 2016080911 | A1 | 5/2016 |
| WO | 2017141024 | A2 | 8/2017 |

OTHER PUBLICATIONS

Korean Office Action and its English translation for corresponding KR Application No. 10-2020-7030210 dated Nov. 26, 2021.
Japanese Office Action for corresponding JP Application No. 2020-551393 dated Aug. 31, 2021.
European Search Report for corresponding EP Application No. 18910356 dated Nov. 9, 2021.
Chinese Office Action and its English translation dated Oct. 7, 2023 of corresponding Chinese Application No. 20180092336.1.

* cited by examiner

BLOOD GLUCOSE TRACKING SYSTEM

CROSS-REFERENCE TO RELATED APPLICATIONS

This application is a divisional of U.S. patent application Ser. No. 16/118,827, filed on Aug. 31, 2018, which claims the benefit of U.S. Provisional Patent Application No. 62/646,510, filed Mar. 22, 2018, each of which is incorporated herein by reference in its entirety.

TECHNICAL FIELD

The present invention generally relates to non-invasive, in vivo blood glucose measurement systems, and more particularly to a personalized subcutaneous blood glucose measurement and tracking system for instantaneous real-time readings of blood glucose values.

BACKGROUND

For decades, attempts have been made to develop a system for "real-time" direct reading, non-invasive measurement of glucose levels in the bloodstream. To date, these efforts have been unsuccessful primarily due to the inherent nature of glucose itself, which readily dissolves in blood, as well as the containment of the bloodstream in the human body, making a direct, non-invasive measurement of glucose residing in the bloodstream extremely difficult.

Historically, optical methods have been favored in attempts to measure blood glucose levels utilizing visible light, infra-red light, or by attempting to detect polarization changes caused by varying glucose levels in the blood. These efforts have been repeatedly proven fruitless, as were other attempts at direct, non-invasive measurement of blood glucose levels.

Presently available continuous blood glucose monitoring systems, in reality, actually measure interstitial fluid glucose levels rather than directly measuring blood glucose levels. As a result, such "blood glucose" systems or meters do not provide "real time" blood glucose readings. In addition, such systems inherently suffer from a substantial time lag—generally about 20 minutes with the correlation of interstitial fluid measurements relative to blood glucose readings.

Although generally recognized that blood glucose levels have been able to be measured fairly accurately via microwave means in vitro under controlled laboratory conditions, prior art measuring equipment has lacked the ability to make these measurements in vivo. While clinically useful measurements may be possible in such fixed laboratory conditions, a mechanism and embodiment that allows for actual non-invasive blood glucose readings "in the field" has heretofore not existed, to say nothing about the automatic calibration mechanisms that are needed to develop these simple laboratory measuring devices into a system that is suitable for everyday use with actual living beings who exhibit individual variations and characteristics from one another.

In view of the foregoing, there is a need for an actual (direct reading) blood glucose measurement system that is non-invasive and can be used in vivo without exhibiting the inherent measurement variation and time lag to determine blood glucose measurements generally associated with prior art "blood glucose" meters that are actually "interstitial fluid" measuring devices. Accordingly, it is a general object of the present invention to provide a novel blood glucose tracking system that provides a new, optimized and efficient approach to blood glucose measurement, tracking and monitoring, that is non-invasive, directly measures blood glucose, and can be done in vivo without measurement variation and time lag.

SUMMARY

The present invention, directed to a blood glucose tracking system and method, works differently than prior art "blood glucose" meters and prior attempts at non-invasive measurement devices. Instead of trying to duplicate the specialized and optimized equipment needed to measure the glucose level of a solution in a controlled laboratory setting, the present invention achieves an accurate calculation of said glucose level directly from the bloodstream by measuring how much overall emitted microwave energy is transmitted to and subsequently accepted by blood vessels in a defined and fixed target area, and then comparing this instantaneous measurement value against a prior calibration value. The difference between the instantaneous power reading measurement and the prior calibration power reading measurement is analyzed and calculated to determine a resultant blood glucose value, which may further be acclimatized through additional sensed values that compensate for varying biological or ambient factors or changes relative to the individual patient. Still further, the determined blood glucose value can be displayed for reading and/or transmitted and stored for recording for future reference.

Unlike all presently available continuous "blood-glucose" meters (which, as noted above, actually measure interstitial fluid rather than blood glucose directly), the blood glucose tracking system in accordance with the present invention actually reads the instantaneous glucose concentration in a bloodstream. Additionally, unlike prior art meters that read interstitial fluid, the system reads and provides a blood-glucose value in real time without any time lag between measurement and actual blood-glucose readings. Still further, such real time measurements allow the blood glucose levels to be measured and monitored in vivo utilizing a compact measurement unit that can preferably be worn by the individual for in vivo use.

The system and method of the present invention is inherently different to other prior art systems and methods mainly in that the present invention relates to a direct absorptive measuring system, and uniquely does not depend on measuring transmitted energy that has been transmitted from a transmitting element through layers of skin and/or other body parts to a receiving element.

In accordance with preferred embodiments of the present invention, the system and method of blood glucose measurement utilizes a short duty-cycle, high impulse power/very-low average-power microwave energy source, preferably transmitting radio frequency energy. Blood composition averages about 92% water overall. It is a known fact that water-containing glucose absorbs microwave energy to an extent greater than water without glucose. By exploiting this phenomenon, there exists a practical pathway to finally being able to non-invasively detect and measure the instantaneous in-vivo level of glucose in the bloodstream. In accordance with preferred embodiments, the microwave energy from the energy source is fed into an antenna assembly designed to focus and transmit this energy toward appropriate subcutaneous blood vessels, namely, those blood vessels that are closest to the surface of the skin. In further preferred embodiments, the energy source and antenna assembly are provided in a housing mountable to the patient's body proximate subcutaneous blood vessels to be measured in a desired target area, more preferably mountable to the patient's arm, and even more preferably mountable to the patient's wrist, for example, as part of a bracelet or watch.

A unique and important part of the system and method of blood glucose measurement in accordance with the present invention is the use of an individually tailored Radio frequency (RF) mask for each target patient and that individual's desired target area. Such an RF mask permits the transmitted microwave energy to reach only an exactly outlined target area of interest, such as, specific segments of near-surface blood vessels. Moreover, the microwave energy may be further contained, shaped and exclusively directed to a location and depth confirming to a specifically defined area that contains said "near surface" blood vessels by optimizing the antenna radiation lobe pattern(s), transmitted frequencies chosen, and power levels used. The same RF mask that limits the area(s) to which RF energy is directed and allowed to be transmitted also inherently limits the measurements of energy that otherwise would be absorbed outside of the desired target area, thus greatly increasing the accuracy of readings using the system and method of the present invention.

In an aspect of the present invention, the microwave energy is contained, shaped, and exclusively allowed to be directed towards a desired target area to a depth in a confirming specific area that contains subcutaneous blood vessels. The antenna assembly is preferably located adjacent to the desired target area. In embodiments, the antenna radiation lobe patterns, transmitted frequencies, and power levels can be varied with respect to specific patients and target areas on said patients.

In preferred embodiments of the present invention, the power levels needed to reach the targeted subcutaneous blood vessels are achieved by using pulsed-type radio wave emissions, similar to those used by radar transmitters.

In accordance with embodiments of the present invention, with each calibration, a known glucose value and its corresponding delivered power value could be placed into a memory buffer. As the test subject's glucose level changes, this would result in the average power level accepted by the bloodstream through the system to either rise or fall in value relative to a power value associated with the last calibration value. With each subsequent periodic microwave emission, the measurement unit would record all new data, and calculate blood glucose values based on an extrapolation of the change in the delivered/accepted power level between the instantaneous power level and previous calibration values.

Objects, features and advantages of the present invention will become apparent in light of the description of embodiments and features thereof, as enhanced by the accompanying figures.

BRIEF DESCRIPTION OF THE DRAWINGS

FIG. 6 illustrates a mask used on a patient to limit the area(s) to which energy transmitted from a measurement device in accordance with the present invention is allowed to be transmitted to.

DETAILED DESCRIPTION

Figure 1:
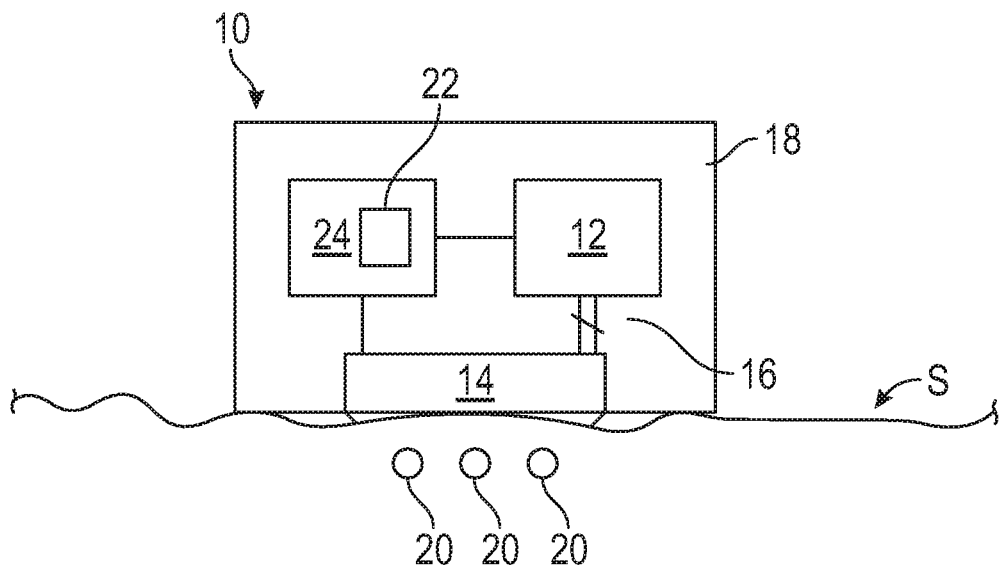
FIG. 1 illustrates a schematic embodiment of a blood glucose tracking system in accordance with the present invention for non-invasive in vivo blood glucose measurement.

Referring to FIG. 1, a schematic embodiment of a blood glucose tracking system for non-invasive in vivo blood glucose measurement in accordance with the present invention is illustrated. The system generally comprises a measurement unit 10 having a microwave energy source (such as a transmitter 12) operatively connected to an antenna assembly, generally comprising an antenna 14, via coaxial cable or a waveguide, generally represented as reference numeral 16. The transmitter 12 and the antenna 14 may be disposed within a common antenna housing 18, as illustrated, or disposed in separate units, provided that they are operatively connected with one another. The antenna assembly also preferably comprises a controller/processor 24, which is used to measure the amount of power/energy delivered through the antenna 14. The transmitter 12 may also be in operative communication with the controller 24.

The transmitter 12 comprises a very-low average-power microwave energy source and short duty-cycle, high-impulse power, preferably transmitting radio frequency energy, and more preferably emitting pulsed-type radio wave emissions similar to those used by radar transmitters. The transmitter 12 feeds into the antenna 14 for focusing and transmitting microwave energy towards appropriate subcutaneous blood vessels 20 located at a desired target area 50 on the patient. In use, the measurement device 10 measures the microwave energy absorbed in the near-by blood vessels 20 to aid in determining the blood glucose levels in the target area 50. More particularly, the controller 24 measures the power delivered to the blood vessels 20 by determining how much energy generated by the transmitter 12 is outputted by the antenna 14. As illustrated in FIG. 1, the antenna housing 18 is placed on or near the patient's skin S proximate to subcutaneous blood vessels 20 for measurement, such as on the patient's wrist.

Figure 7:
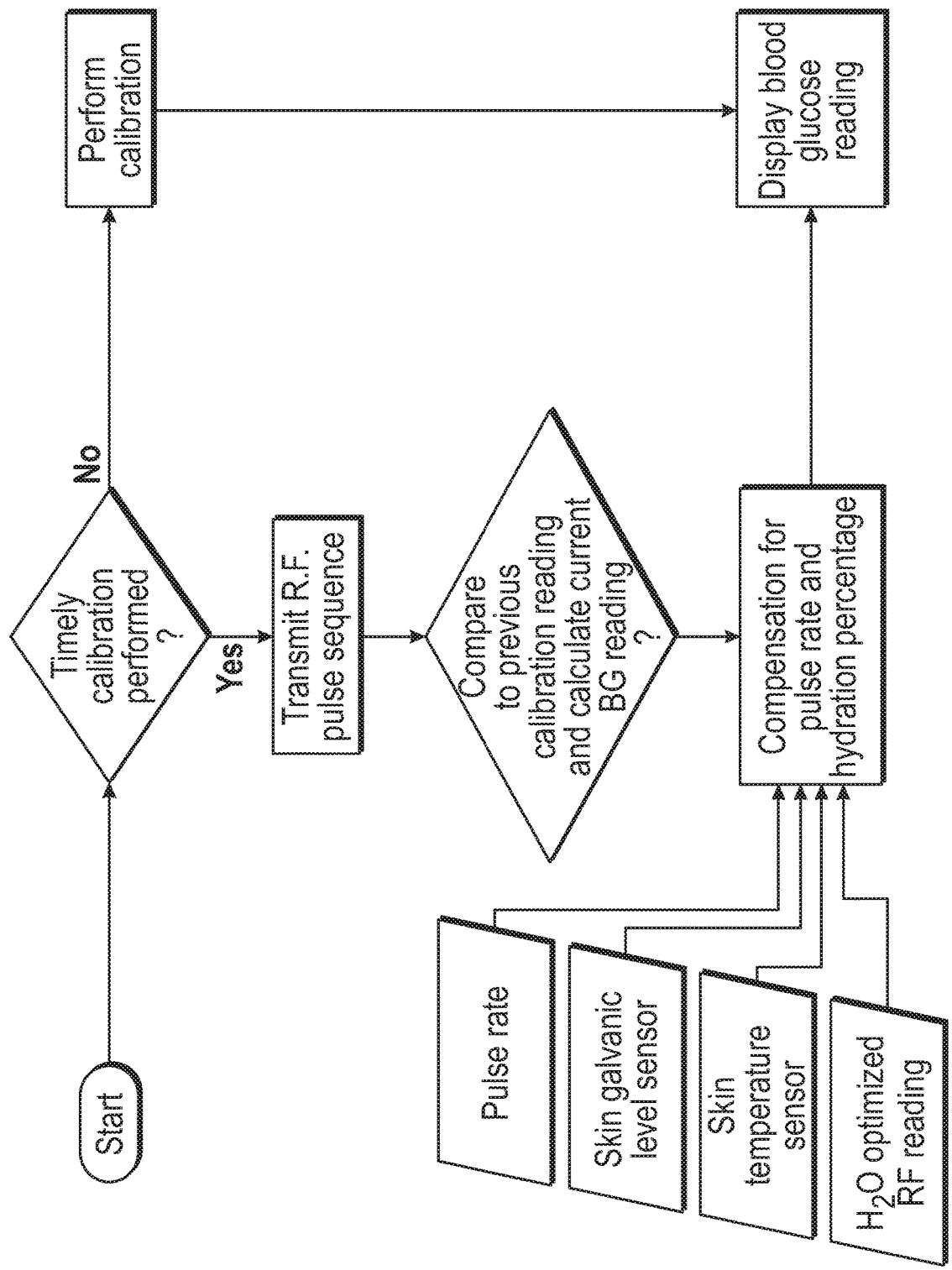
FIG. 7 provides a flow chart illustrating a test sequence in accordance with preferred embodiments of the present invention.

Referring to the schematic illustration of FIG. 7, the system achieves an accurate calculation of the patient's blood glucose levels in a defined and fixed target area 50 by measuring how much overall emitted microwave energy is transmitted to and accepted by subcutaneous, or "near surface", blood vessels 20 in the target area 50, preferably by absorption therein. Instantaneous, real-time measurement values, taken directly from the bloodstream, can be compared with a pre-determined calibration value. The difference, or "delta" value, between the measurement value and the calibration value can provide, via analysis and calculation, a resultant blood glucose value. In preferred embodiments, an algorithm correlating power energy values with blood glucose values is used to determine the resultant blood glucose value. Such an algorithm is preferably stored in the controller 24. The calibration value can be stored in a memory buffer 22, provided as part of the controller 24.

The desired subcutaneous blood vessels 20 for accurate measurement in accordance with the present invention are typically found near the wrists of individuals, though the system of the present invention can also be used with other parts of the body without departing from the spirit and principles of the present invention. Accordingly, the antenna 14 is preferably located adjacent to a desired target area, preferably by placing the antenna housing 18 on the skin surface S proximate to the desired target area 50. A unique and critically important part of the system of the present invention is the use of individually-tailored RF masks 52, generally illustrated in FIG. 6, for each target patient and desired target location 50 that permits the microwave energy delivered by the antenna 14 to only reach an exact outlined target area(s) of interest, such as specific segments of near-surface blood vessels 20. By further optimizing the antenna radiation lobe pattern(s), transmitted frequencies chosen, and power levels used, the microwave energy is further contained, shaped, and exclusively directed to a depth in a confirming specific area that contains said "near surface" blood vessels 20. As the skin S in these areas is exceedingly thin, not only is it easy to actually see the blood vessel locations, but it should be also noted that these areas have almost nothing in the pathway between the antenna 14 and the targeted blood vessels 20 to unduly attenuate or interfere with the transmission path.

The system and method of the present invention is inherently different to other prior art systems and methods in that the present invention is a direct absorptive measuring system, and uniquely does not depend on measuring transmitted energy that has been transmitted from a transmitting element through layers of skin and/or other body parts to a receiving element.

Figure 6:
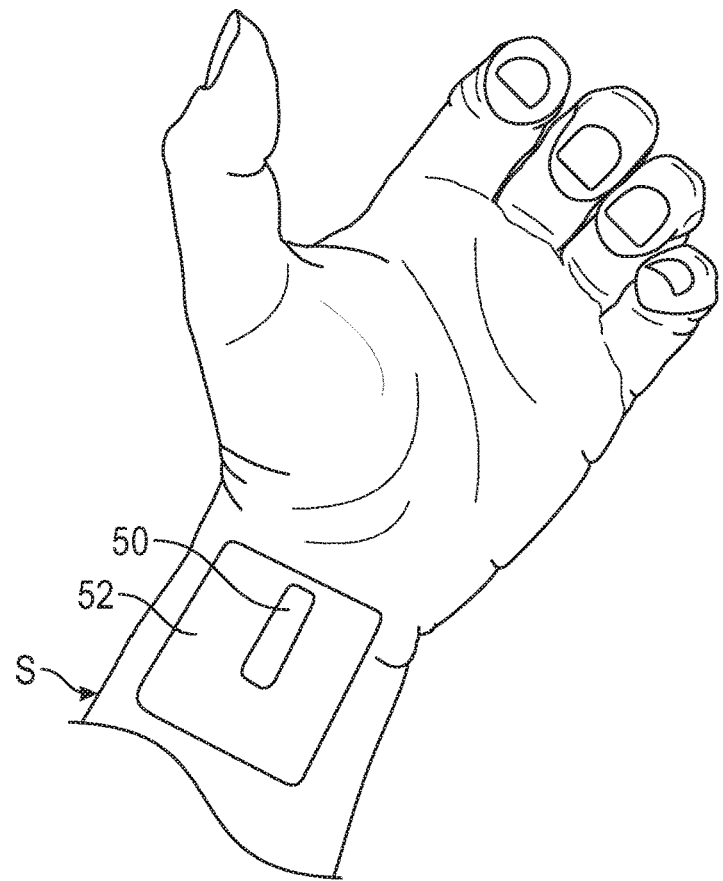

In use, an RF mask 52 is created for an individual patient, and then laid on and temporarily adhered to the patient's skin S over the desired target area 50, as generally illustrated in FIG. 6, and then used with the measurement unit 10 described herein for blood glucose measurement and tracking. The same RF mask 52 that limits the area(s) to which the RF energy is allowed to be transmitted also inherently limits the measurements of energy that otherwise would be absorbed outside of the target area 50, thus greatly increasing the accuracy of readings. Preferred methods for creating individualized RF masks 52 are described in more detail below.

As noted, the power levels needed to reach the targeted subcutaneous blood vessels 20 are achieved by using pulsed-type radio wave emissions, similar to those used by radar transmitters. Although the "peak" power levels may be relatively high (in order to penetrate the skin to the depth necessary), the duty cycle of these emissions is quite low, which results in the "average" power level being quite low. This makes such a wireless transmitter 12 not only very energy efficient, but also such emissions do not result in any perceptible temperature rise by the individual wearing such a system, as opposed to continuous wave emissions that are typically used in laboratory equipment.

The extrapolation process of determining the amount of energy absorbed (e.g., the power reading measurement) may utilize one or more of the following processes, either alone or in combination:

In a first approach, the antenna assembly measures one of delivered forward emitted peak power level and/or average power levels at a specific radio frequency over a specific time frame. More specifically, as the microwave pulses are emitted from the antenna 14, their peak transmitted power level and/or average power level are measured by the controller 24. Then, the "delta" value for the measured transmitted energy power level in comparison to a calibration value recorded at the time of the last calibration reading/measurement is determined. The system identifies, via an algorithm, a new calculated blood glucose reading that corresponds to the measured energy power levels. More particularly, the algorithm correlates specific blood glucose levels with energy absorption data. The calculated/determined blood glucose reading can be provided to a display and/or memory buffer, as desired.

In a second approach, instead of reading the forward power level actually delivered and/or accepted by the target blood vessels 20, the system measures the reflected energy power levels in the blood vessels 20 of the desired target area 50 to determine a "delta" value in comparison with a calibration value. In this case, lower reflected power readings would indicate a greater energy acceptance in the target area 50, which would, in turn, indicate and track with higher glucose levels. The higher the levels of glucose in the blood, the greater willingness for the blood to absorb energy, which would reduce the reflected power. As with the first approach, the calculated "delta" value, the system identifies, via the algorithm, a new calculated blood glucose reading. The calculated/determined blood glucose reading can be provided to a display and/or memory buffer, as desired.

In a third approach, the system measures Standing Wave Ratio (SWR) readings from the transmitter 12 at a specific radio frequency and from such a measurement, calculates a "delta" value in relation to calibration readings. In this case, SWR readings generally track blood glucose levels, wherein the SWR readings rise with lower levels of blood glucose, and decrease with higher levels. The calculated "delta" value is again used, via the algorithm, to determine the appropriate blood glucose reading, when can be provided to a display and/or memory buffer, as desired.

The various processes listed above have all of their power measurements taking place at a fixed frequency. In accordance with a fourth approach, the transmitter 12 is commanded to sequentially vary its transmission frequency in a pre-determined fashion, frequency stepping in a repeating low-to-high, or high-to-low fashion, within a predetermined frequency range. The amount of energy acceptance from each of the individually transmitted radio frequencies utilized would be measured for either peak or average power delivered, and then compared to the other frequencies in the same measurement cycle. The shift in the absorption rate between frequencies would track changing glucose levels, and would be extrapolated to a blood glucose value using one or more extrapolation methods. One embodiment that can be used with this method would dynamically analyze the location of the frequency that accepted maximum energy absorption, which would then become the "center" or "index" frequency. This "index" frequency would be compared to the last calibration "index" frequency, to create an offset value. This offset value would be applied to a scaling algorithm to determine a calculated blood glucose value, which can then be provided to a display and/or memory buffer, as desired.

A similar approach may utilize the frequency hopping method of the fourth approach, but rather than solving for and analyzing a "center" or "index" frequency, this approach would instead analyze the energy changes in all of the various transmitted frequencies to indicate the "spread" or bandwidth of those frequencies that showed microwave energy absorptive activity above a predetermined threshold, and then compare the instantaneous spread of those frequencies above the threshold with the spread of the readings obtained at the last calibration. An algorithm would analyze the increase or decrease of the spread to come up with a difference value, and this value would be applied to an algorithm to calculate a blood glucose reading, which can then be provided to a display and/or memory buffer, as desired.

With each subsequent periodic microwave emission, the measurement unit 10 would record all new data, and determine a blood glucose value based on an extrapolation of the change in the delivered/accepted power level between the instantaneous power level and the previous calibration value. As an example, if the calibration entry resulted in a direct blood glucose reading of 100 and the blood at that glucose level had accepted 100 milliwatts of power from the transmitter 12 (assuming the system were using a 1:1 algorithm), a new test reading showing a 10% rise in the power delivered to the target area 50, or 110 milliwatts, would calculate to a blood glucose level of 110 mg/dl.

In addition to the base transmitter 12 and power sensing via the antenna assembly, the blood glucose tracking system and method in accordance with the present invention, can utilize additional optional compensation methods to enhance the accuracy of the blood glucose readings. Among these methods are the following:

(A) A pulse rate sensor incorporated to compensate for change in the rate of blood flow through the blood vessels 20. A faster or slower blood flow would alter the rate of energy acceptance, and could detrimentally skew the calculated results. To compensate for this, a pulse rate sensor would be optionally incorporated to allow a dynamic compensation for this variable.

(B) A skin temperature sensor in close proximity to the desired target area 50 allows for temperature compensation to be applied to optimize for changing blood vessel diameters (e.g., vasodilation; vasoconstriction) due to body core temperature variations.

(C) By measuring the skin galvanic response, this measurement, preferably along with the skin temperature monitor, can determine the level of sweat production in the area of the measurement unit 10, which could skew the microwave absorption rate. As a result, the system can compensate for sweat production based on measurement of skin galvanic data.

(D) Although blood generally averages 92% water, there are times when the hydration levels of the patient may vary widely. A periodic microwave energy measurement at a frequency more resonant for water (as opposed to one more resonant to glucose) could be used to continuously calibrate the measurement unit 10 to account for varying hydration levels of the patient. Either dual band microwave transmitters, or a wideband single band transmitter which is capable of operating at wide frequency variances would allow one frequency or transmitter to be dedicated to monitoring water levels, while the other frequency or transmitter would be optimized for glucose detection, in the manner described above.

Figure 2:
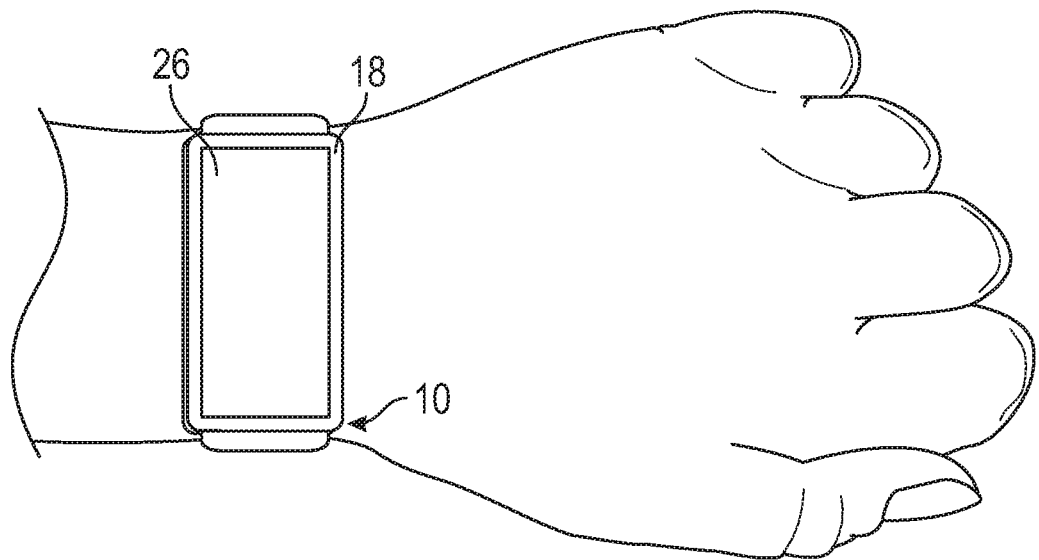
FIG. 2 illustrates another embodiment of the blood glucose tracking system in accordance with the present invention, whereby the system is embodied in a wristwatch.
Figure 3:
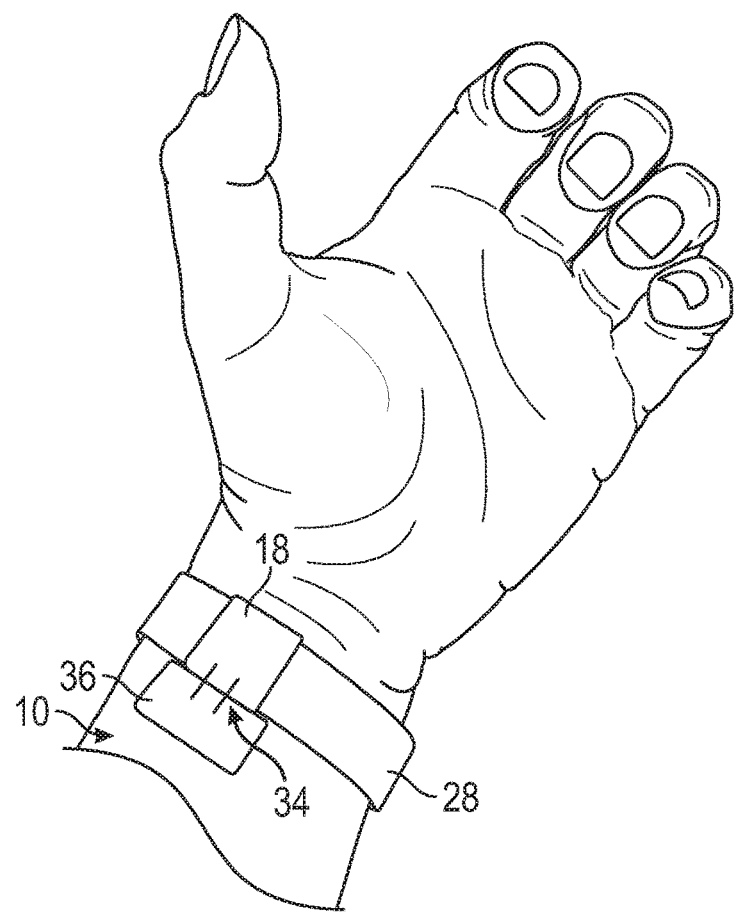
FIG. 3 illustrates yet another embodiment of the blood glucose tracking system in accordance with the present invention, whereby an auxiliary housing, including an antenna, is connected to a watch or bracelet housing a wireless transmitter, ideally worn on a wrist.
Figure 4:
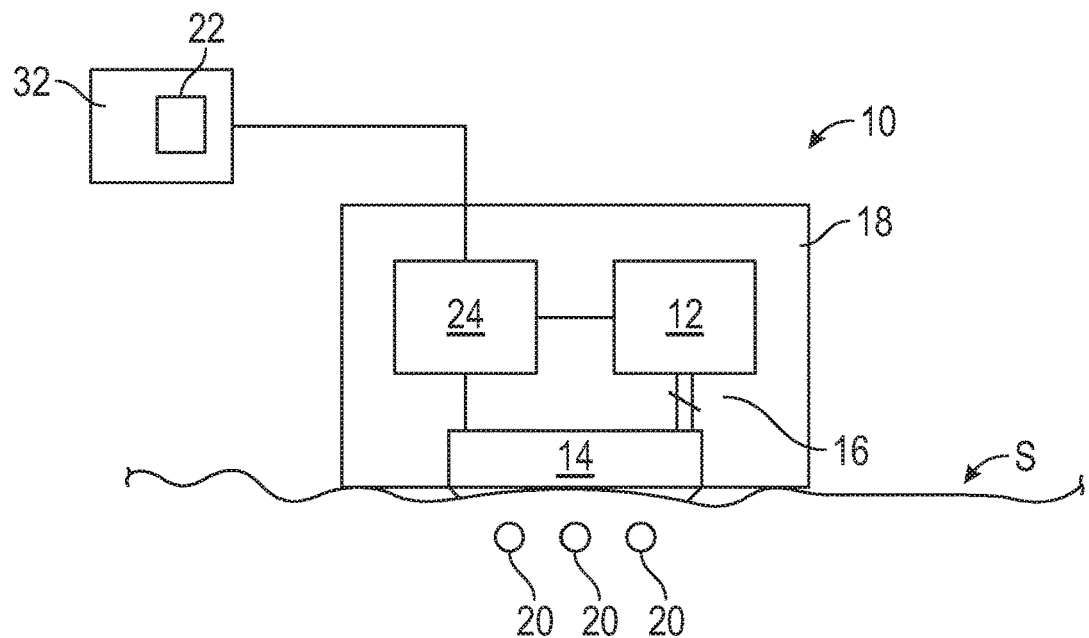
FIG. 4 illustrates a schematic embodiment of a blood glucose tracking system whereby data related to determined blood glucose levels is provided to a computer, display, or memory buffer, as desired.
Figure 5:
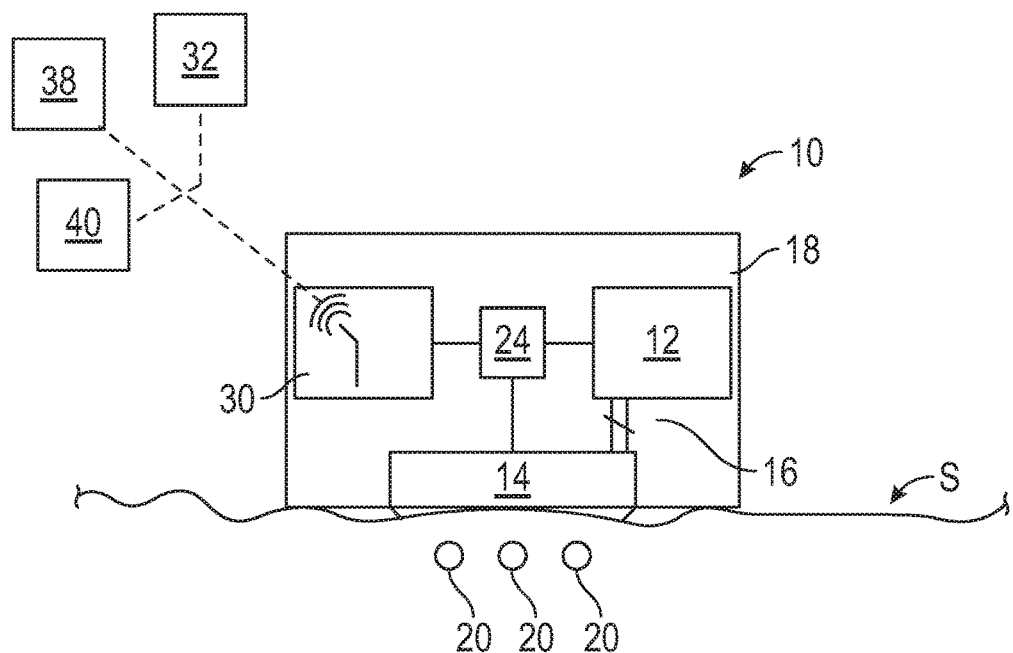
FIG. 5 illustrates another schematic embodiment of a blood glucose tracking system involving two transmitters.

Additional measurement and display means can be provided with the measurement unit 10. For example, a display screen 26 can be provided on the antenna housing 18, as illustrated in FIGS. 2 and 4. Additionally, the measurement unit 10 can be part of or take the form of a bracelet or watch 28 worn around the wrist, for example, by an adhesive. Additional transmitter means 30 can further be included, as schematically illustrated in FIG. 5, to transmit data from the measurement unit 10 to another unit 32, such as a computer, tablet or smart phone, for display and/or recording of blood glucose measurements taken by the measurement unit 10. For example, a measurement unit 10 in the form of a bracelet or watch 28 could store measured data, and then sync with a computer 32 for additional storage, monitoring and analysis of a patient's blood glucose measurements.

The blood glucose tracking system in accordance with the present invention may be a discrete "stand-alone" system, such as described above and illustrated in FIG. 1, or may be incorporated into an unrelated item worn on the wrist (such as a watch or jewelry) to take advantage of the near-surface blood vessels 20 of the wrist in a non-apparent fashion. In the instance of a watch 28, which would contain the transmitter 12 and its associated control components, a small fixed or flexible section of miniature waveguide 34 could be attached to the body of the watch 28, while the other end would connect to a detachable auxiliary "side car" antenna housing 36 placed over the desired target area for measurement. Thus, such an auxiliary antenna housing 36, including the antenna 14 and its associated control components 24, could be attached to the watch 28 for measurements, and detached when not needed. When the housings 18 and 36 are attached, the antenna 14 can be connected to the transmitter 12 via a waveguide or coaxial cable 34 running through the band of the watch 28. In the case of a watch or "smart watch" as illustrated in FIG. 2, in which a blood glucose tracking system in accordance with the present system may be incorporated as an integral part thereof, the existing digital readout 26 of the watch 28 could be used to display instantaneous blood glucose readings.

Numerous other creative physical embodiments may be utilized without departing from the spirit and principles of the present invention, for example, by incorporating a metal shield to limit the antenna energy towards an adjacent desired target area 50, or batteries to power the RF transmitter 12 or other equipment located within the watchband segments.

The system may also incorporate a separate data transmitter 30 (which, as noted above, is in addition to the sampling transmitter 12) to relay the raw or calculated data output to a separate display 32 or storage device 38, such as a computer, tablet or smart phone, or to a device such as an insulin pump 40. Depending on the manufacturer or model of such devices, the data output would be sent in the appropriate proprietary format for, as noted, display and/or storage.

The system and method in accordance with the present invention derive instantaneous blood glucose readings by comparing differences between a "control" reading, in which the blood glucose value is known, with an instantaneous reading, in which the blood glucose value is not known and needs to be determined. The "control" reading can be a calibration value, which can be adjusted after each such calibration measurement using the system (e.g., a new control measurement value becomes the calibration value for the next measurement). In order to accurately extrapolate the instantaneous glucose readings with the level of microwave energy accepted, a periodic calibration performed by an appropriate measurement method, such as by utilizing a traditional "finger stick" blood glucose testing method, or other means of accurately determining actual blood glucose levels. This data would provide the measurement unit 10 with a standard reference measurement, which would then be used to compare subsequent readings for a specific body and body target location (such as certain blood vessels in a wrist) in an individual to provide and track subsequent blood glucose readings.

In order to create unique individualized RF antenna masks 52, such as illustrated in FIG. 6, two preferred methods of mask creation may be utilized. The first, a "manual" method, utilizes a thin piece of Mylar or other flexible transparent material that is temporarily wrapped around an individual's wrist or other location associated with a desired target area 50, and held in place. A marking pen is used to outline the exact target area 50 for the antenna 14, along the width of the subject's arm or other body part, to provide subsequent positioning reference guidance. After removal, the flexible sheet is laid over a blank antenna mask and the overlay is used to guide the cutting of the mask opening area. Once the RF mask 52 is created, it can be laid on and temporarily adhered to the patient's skin S at the desired target area 50, and used with the measurement unit 10 described herein for measurement and tracking of blood glucose levels.

The second preferred RF mask creation method is an "automatic" method by which the desired target area 50 is photographed or scanned in the visible and/or thermal infrared spectrum. The thermal data can further be used to establish the best sensing areas. A physical measurement is also made of the general area surrounding the desired target area 50. The resulting photo data is fed into a laser cutting machine or CNC machine that scales the cutting information based upon the measurements, and then automatically selects and outlines the unmasked area to correspond to the optimized target are criteria. The cutting machine(s) can directly create a mask opening on a non-RF transmissive material sheet. This automatic selection process may be as a result of either the gathered visible information or the gathered IR thermal information, or both.

The foregoing description of embodiments of the present invention has been presented for the purpose of illustration and description. It is not intended to be exhaustive or to limit the invention to the form disclosed. Obvious modifications and variations are possible in light of the above disclosure. The embodiments described were chosen to best illustrate the principles of the invention and practical applications thereof to enable one of ordinary skill in the art to utilize the invention in various embodiments and with various modifications as suited to the particular use contemplated.

What is claimed is:

1. A blood glucose measurement device comprising:
    an antenna housing having an antenna assembly disposed therein, said antenna housing being adapted for placement on or near a patient's skin proximate to a desired target area comprising blood vessels to be measured, and said antenna assembly comprising an antenna;
    a transmitter operatively connected to the antenna for transmitting microwave energy into the blood vessels of the target area via the antenna; and
    a controller operatively connected to the transmitter;
    wherein controller is configured to:
        establish a calibration value of microwave energy absorption by blood located within blood vessels that are within the target area;
        determine a measurement value based on an amount of energy transmitted by the transmitter and absorbed by blood vessels in the target area;
        compare the calibration value with the measurement value to determine a calculated power differential value; and
        determine a blood glucose value representative of the calculated power differential value.

2. The blood glucose measurement device according to claim 1, wherein the controller is configured to identify a difference between the calibration value and the measurement value for determining the calculated power differential value.

3. The blood glucose measurement device according to claim 1, wherein the blood vessels in the target area are subcutaneous blood vessels.

4. The blood glucose measurement device according to claim 1, wherein the measurement device is adapted to be placed on the patient's arm proximate the target area.

5. The blood glucose measurement device according to claim 4, wherein the measurement device is adapted to be placed on the patient's wrist.

6. The blood glucose measurement device according to claim 4, further comprising a strap to which the antenna housing is attached, said strap being adapted to be wrapped around the patient's arm.

7. The blood glucose measurement device according to claim 1, further comprising a visual display for displaying measurement data corresponding to the absorbed microwave energy measurement value.

8. The blood glucose measurement device according to claim 1, further comprising a second transmitter for transmitting measurement data to an external device for at least one of display and storage of the measurement data.

9. The blood glucose measurement device according to claim 1, wherein the microwave energy is in the form of microwave pulses.

10. The blood glucose measurement device according to claim 1, wherein the controller is configured to determine actual energy power levels delivered to the blood vessels in the target area from the antenna assembly.

11. The blood glucose measurement device according to claim 1, wherein the controller is configured to determine reflected energy power levels delivered to the blood vessels in the target area.

12. The blood glucose measurement device according to claim 1, wherein the controller is configured to determine a standing wave ratio reading representative of energy absorption in the blood vessels in the target area.

13. A blood glucose measurement device comprising:
    an antenna housing having an antenna assembly disposed therein and comprising an antenna;
    a transmitter operatively connected to the antenna for transmitting microwave energy into blood vessels of a target area via the antenna; and
    a controller operatively connected to the transmitter;
    wherein controller is configured to:
        establish a calibration value of microwave energy absorption by blood located within blood vessels that are within the target area;
        determine a measurement value based on an amount of energy transmitted by the transmitter and absorbed by blood vessels in the target area;
        compare the calibration value with the measurement value to determine a calculated power differential value; and
        determine a blood glucose value representative of the calculated power differential value.

14. The blood glucose measurement device according to claim 13, wherein the controller is configured to vary a transmission frequency of the microwave wave energy within a predetermined frequency range.

15. The blood glucose measurement device according to claim 13, wherein the blood vessel in the target area is a subcutaneous blood vessel.

16. The blood glucose measurement device according to claim 13, further comprising an individualized radio frequency mask that is transmissive only in a precise area that correlates to the size, shape and location of the blood vessels.

17. The blood glucose measurement device according to claim 13, wherein the antenna housing is adapted to be located on a patient's wrist, arm, ankle, or other bodily location that has blood vessels in close proximity to the skin's surface.

18. The blood glucose measurement device according to claim 13, further comprising a display, wherein the controller is configured to cause the display to display the determined blood glucose value.

* * * * *